United States Patent [19]
Park et al.

[11] Patent Number: 5,656,142
[45] Date of Patent: Aug. 12, 1997

[54] BIOSENSOR FOR MEASURING GAS AND THE MANUFACTURING METHOD THEREOF

[75] Inventors: Je Kyun Park, Seoul; Hee Jin Lee, Kyunggi-Do, both of Rep. of Korea

[73] Assignee: Goldstar Co., Ltd., Seoul, Rep. of Korea

[21] Appl. No.: 276,097

[22] Filed: Jul. 15, 1994

[30]  Foreign Application Priority Data

Jul. 16, 1993 [KR] Rep. of Korea .................. 93-13482

[51] Int. Cl.$^6$ .................................................. G01N 27/26
[52] U.S. Cl. ................... 204/403; 204/412; 204/418; 204/415; 204/414; 435/817; 435/287.9; 435/287.5; 435/287.1
[58] Field of Search ......................... 204/403, 412, 204/418, 415, 435, 414; 435/817, 291, 288

[56] References Cited

U.S. PATENT DOCUMENTS

| | | | |
|---|---|---|---|
| 4,225,410 | 9/1980 | Pace | 204/153.12 |
| 4,980,043 | 12/1990 | Tomita et al. | 204/414 |
| 5,093,236 | 3/1992 | Gonzales-Prevatt et al. | 435/9 |
| 5,162,525 | 11/1992 | Masilamani et al. | 540/468 |
| 5,264,103 | 11/1993 | Yoshioka et al. | 204/403 |

*Primary Examiner*—John Niebling
*Assistant Examiner*—Bruce F. Bell
*Attorney, Agent, or Firm*—Oppenheimer Poms Smith

[57] ABSTRACT

A biosensor for measuring gas-phase organic chemicals rapidly and accurately. The biosensor includes a thick film electrochemical device having an insulating substrate, electrodes formed on the substrate, connecting pads for the electrodes and an insulating layer, and a responsive membrane formed on the electrode portion of the electrochemical device. The responsive membrane is provided with a moisture-absorbing gel layer in which an enzyme for reacting with the gas-phase organic chemical is immobilized.

11 Claims, 3 Drawing Sheets

F I G. 1A
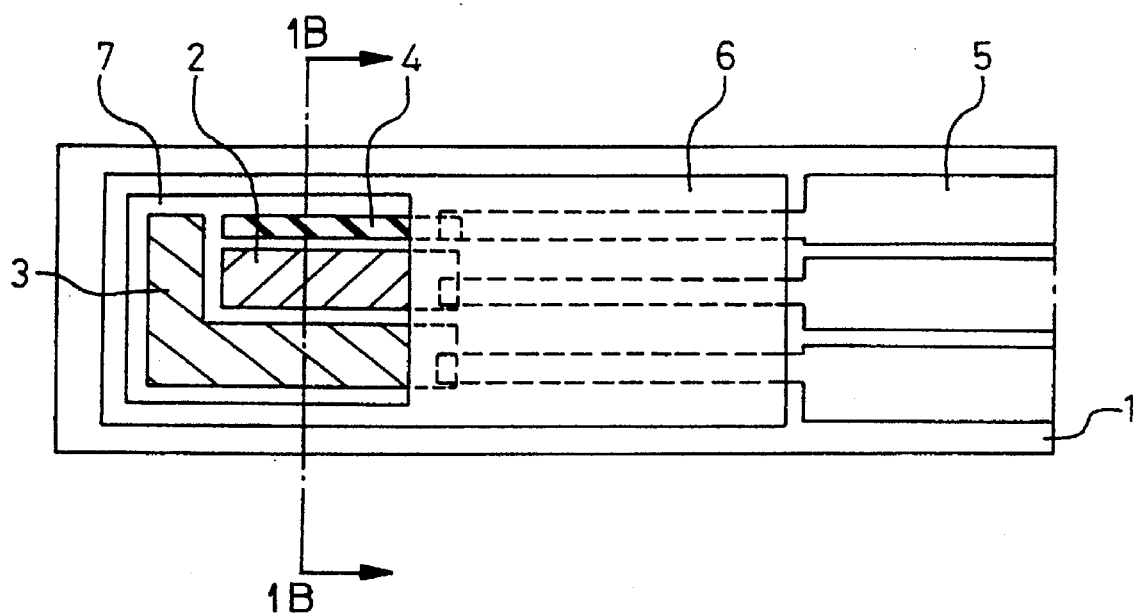
F I G. 1B
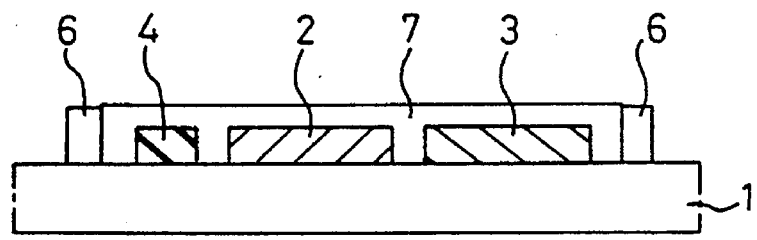

BIOSENSOR FOR MEASURING GAS AND THE MANUFACTURING METHOD THEREOF

BACKGROUND OF THE INVENTION

1. Field of the Invention

The present invention relates to a biosensor for measuring gas, and more particularly to an enzymatic gas biosensor and the manufacturing method thereof, which can measure oxidization of a gas-phase organic chemical by enzymatic reaction, utilizing a thick film electrochemical device.

2. Description of the Prior Art

Conventionally, electrochemical measurement type biosensors have been made by immobilizing, as a membrane, enzymes or micro-organisms on the surface of an electrode such as an $H_2O_2$ electrode, an oxygen electrode, an ammonium ($NH_4+$) ion-selective electrode, etc., or of an ISFET (ion-selective field effect transistor). Such type of biosensor can detect and measure an electrode-active material formed as the result of a single or multi-step enzymatic reaction. U.S. Pat. No. 4,655,880 discloses such a biosensor in which various kinds of oxidase materials are immobilized on a thick film electrochemical device to measure electrode-active materials.

Meanwhile, biosensors utilizing oxide-semiconductors are now widely used for measuring gas-phase chemicals, which measure the change of conductivity when reducing gas such as methane, carbon monoxide, etc. is oxidized on the surface of the sensor.

In the fields of a gas-solid bioreactor and the analysis thereof, conversion reaction of a gas-phase organic chemical by a dried enzyme has now been an important theme for study, and there has been great amounts of research for its application in the field of biotechnology. For example, a bioreactor in which alcohol dehydrogenase and NAD (β-Nicotinamide adenine dinucleotide) or NADH (the reduced form of NAD) are treated with albumin and glutaraldehyde has been developed to form a gas-phase product by utilizing a gas-phase substrate (Biotechnol. Letters. 8(11): 783–784). Also, another bioreactor in which alcohol oxidase and catalase are adsorbed to DEAE-cellulose (diethyl aminoethyl-cellulose) or controlled pore glass (CPG) has been developed for a similar purpose (Biotechnol. Bioeng. 34:1178–1185).

Sensors and methods for measuring gas-phase organic chemicals utilizing enzymes are known in the art. U.S. Pat. No. 4,525,704 discloses an enzymatic toxic gas sensor utilizing the fact that the activity of enzymatic reaction is inhibited due to the existence of a toxic material such as an organic phosphoric pesticide. International Application No. 88/01299 teaches a method of measuring the change of color using a color-forming reagent after immobilizing an enzyme on an organic or inorganic carrier.

An alcohol checker generally adopts a gas sensor, for example, TGS822 gas sensor manufactured by Figaro Co., Ltd., Japan, and thus can measure the concentration of alcohol which is contained in gases generated in human breathing.

Meanwhile, Japanese Patent Publication Nos. Sho 60-196198 and Sho 60-172298 teach measuring methods utilizing enzymatic reaction, whereby alcohol contained in an aqueous solution (or in the human's saliva) is measured using a strip-shaped test paper. According to the method disclosed in International Application No. 88/01299, the concentration of alcohol contained in the gases generated in the human breathing is measured by utilizing the change of color.

However, conventional electrochemical measurement type biosensors have the drawback that they must be used in favorable conditions for bioreaction, i.e., in liquid. Accordingly, in order to measure a gas-phase specimen by means of the biosensor of electrochemical measurement type, a responsive membrane of the biosensor should serve as an immobilizing carrier with moisture properly retained as well as serve as an electrode system. Further, when the biosensor is used to react with a gas-phase specimen, electron transmission between the enzyme-responsive membrane and the electrode should be effected satisfactorily, and thus this requires a high-level electrode manufacturing technique and a high-level enzyme immobilizing technique as well.

The conventional gas biosensor utilizing the oxide-semiconductor also has the disadvantages that if it utilizes alcohol-responsive metal-oxide such as $TiO_2$ and $RuO_2$, it is difficult to quantitate alcohol since its selectivity with respect to alcohol deteriorates.

Meanwhile, a conventional biosensor for measuring a gas-phase organic chemical by utilizing enzymatic reaction can quantitate the chemical accurately because of the substrate specificity of the enzyme itself. However, according to the conventional method of measuring the change of color by utilizing 2,6-dichloroindophenol and so on (International Application No. 88/01299), it is also required to measure the absorbance in order to quantitate the organic chemical, resulting in inconvenient use.

SUMMARY OF THE INVENTION

It is an object of the present invention to provide a biosensor and the manufacturing method thereof, which can measure a gas-phase organic chemical rapidly and accurately, utilizing a thick film electrochemical device and an immobilized enzyme membrane formed thereon.

In order to achieve the above object, the present invention provides a biosensor for measuring gas, comprising:

a thick film electrochemical device having an insulating substrate, a plurality of electrodes formed on the insulating substrate, a plurality of pads electrically connected to the electrodes, respectively, and an insulating layer; and a responsive membrane formed on at least one of the electrodes, the responsive membrane including a moisture-absorbing gel layer in which an enzyme for reacting with a gas-phase organic chemical is immobilized.

For the operation of the thick film electrochemical device, an electrolyte must exist. Salt ions existing in a liquid-phase specimen serve as an electrolyte, and thus there is no problem to form an electrode system. In order to analyse a gas-phase specimen, either of a solid electrolyte and a liquid-phase electrolyte layer should be provided. However, a solid electrolyte such as zirconia cannot be used with an enzyme, while a liquid-phase electrolyte is difficult to be formed on the immobilized enzyme membrane.

According to one aspect of the present invention, an enzyme-immobilized layer formed on a thick film electrochemical device, using a moisture-absorbing gel such as polyacrylamide, alginate, agarose, gelatin including potassium chloride (KCl), etc., and thus the enzyme-immobilized layer itself can serve as an electrolyte as well as a carrier of the enzyme.

As described above, according to the gas biosensor of the present invention, the enzyme-immobilized membrane can be easily formed on the thick film electrochemical device.

Also, since the enzyme membrane of the biosensor is kept in a dry state, a reduction of enzyme activity in the enzyme membrane can be prevented while the biosensor is in custody. Further, the biosensor, according to the present invention, has a high thermal stability and a long life since it is used to react with a gas-phase specimen. Furthermore, unlike other biosensors to be used in an aqueous solution, the biosensor according to the present invention has better signal-to-noise characteristics, while it can measure and analyse the specimen having even a low concentration which is difficult to be measured in liquid. In order to increase the sensitivity of the biosensor, a gas-phase specimen containing moisture may be used, or the temperature of the specimen to be measured may be raised to a higher degree.

BRIEF DESCRIPTION OF THE DRAWINGS

The above abject and other features of the present invention will become more apparent by describing the preferred embodiments thereof with reference to the accompanying drawings, in which:

FIGS. 1A and 1B are views showing the structure of the gas biosensor according to one embodiment of the present invention.

DETAILED DESCRIPTION OF THE PREFERRED EMBODIMENTS

Figure 2A:
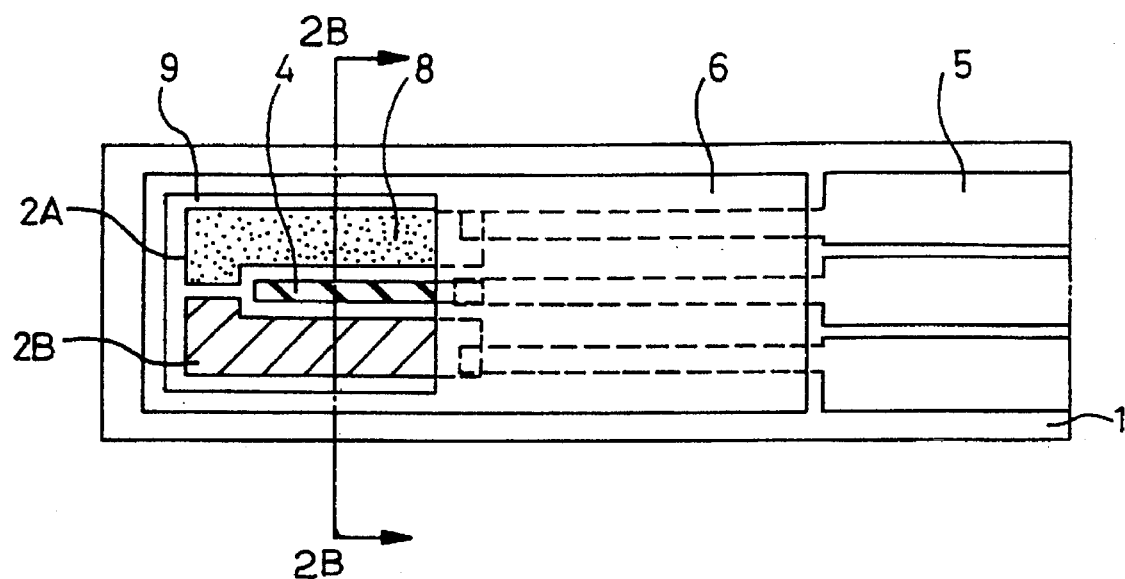
FIGS. 2A and 2B are views showing the structure of the gas biosensor according to another embodiment of the present invention.

FIGS. 1A and 1B show the structure of the gas biosensor according to one embodiment of the present invention. Referring to FIGS. 1A and 1B, the gas biosensor according to the present invention is manufactured by forming an enzyme-immobilized membrane on a thick film electrochemical device.

The thick film electrochemical device can be manufactured utilizing a thick film process whereby a working electrode 2, a counter electrode 3 and a reference electrode 4 are formed on an insulating substrate 1. The insulating substrate 1 is made of alumina ($Al_2O_3$) or high molecular polymer materials such as, PVC (polyvinyl chloride), polyethylene terephthalate, polyethylene, etc., in the course of the thick film process. The working electrode 2 and the counter electrode 3 can be formed by printing on the insulating substrate 1 paste containing electric conductor materials such as platinum (Pt), carbon (C), etc..

In the embodiments, the working electrode 2 and the counter electrode 3 are formed by screen-printing platinum on the alumina substrate (86×84 mm) using a metal screen of 250 mesh, drying the printed material at about 100° C. for about 10 minutes, and then firing it at about 1250° C. The reference electrode 4 is formed by printing silver (Ag) paste or Ag paste containing AgCl, and then firing it at about 850° C.

The electrode characteristics of the electrodes 2,3 and 4 formed as above are not greatly changed according to their arrangements, but the width of the electrode space or the area of the electrode exerts an important effect on the signal and noise levels of the electrode.

Next, connecting pads 5 for electric connection with the respective electrodes 2, 3 and 4 are formed by printing and firing silver/palladium (Ag/Pd) paste on the substrate 1, and then the insulating layer 6 is formed thereon by printing and firing dielectric paste.

In cases where the reference electrode is formed using Ag paste, the Ag/AgCl layer is electrochemically formed on the substrate 1 in a 100 mM $FeCl_3$ solution to complete the thick film electrochemical device. About 20 thick film electrochemical devices are provided on one substrate.

If the electric potential difference of about 650 mV is applied to the working electrode 2 of the completed thick film electrochemical device in comparison with the reference electrode 4, electrode-active materials such as $H_2O_2$ and NADH can be oxidized.

An ethanol biosensor according to the present invention, which is for measuring the concentration of gas-phase ethanol, can be manufactured by applying the following enzyme-immobilizing method on the thick film electrochemical device constructed as above.

First, an enzyme solution is prepared by dissolving 20 mg of an alcohol dehydrogenase enzyme and 6.6 mg of an $NAD^+$ co-enzyme in 1 ml of 0.1M phosphate buffer.

Next, 1 ml of mixed solution is prepared by dissolving 10% (weight/volume) gelatin in 0.1M KCl solution, and then is mixed with 1 ml of the enzyme solution at about 25° C.

5 μl of the enzyme-mixed solution is dropped on the whole electrode portion of each thick film electrochemical device and then is dried, resulting in that a moisture-absorbing gel layer 7, in which the enzyme and the co-enzyme are immobilized, is formed. The thickness of the enzyme-immobilized membrane is determined to be about 50 μm.

An enzyme group of oxidoreductase or hydrolase is used as the above-mentioned immobilized enzyme. Instead of the alcohol dehydrogenase as mentioned above, carbon monoxide dehydrogenase, formate dehydrogenase or alcohol oxidase may also be used.

Also, a similar moisture-absorbing gel layer may be prepared using polyacrylamide, alginate, agarose, etc., instead of the above-mentioned gelatin. But, according to the present invention, the role of potassium chloride used for preparing the moisture-absorbing gel layer is very important to the formation of the electrode system.

Figure 2B:
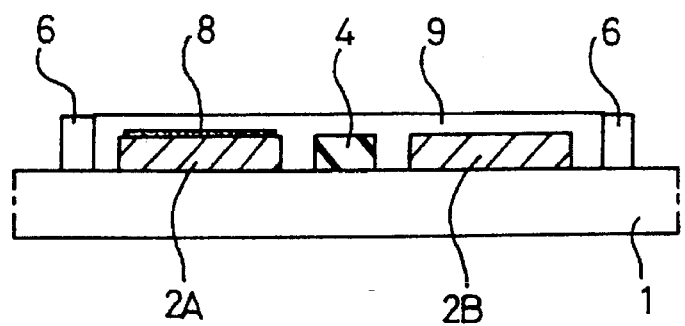

FIGS. 2A and 2B show the structure of the gas biosensor according to another embodiment of the present invention. Referring to FIGS. 2A and 2B, a thick film electrochemical device can be manufactured by forming on an insulating substrate 1 two working electrodes 2A and 2B, a reference electrode 4, connecting pads 5 and an insulating layer 6. An enzyme membrane 8 is formed only on the working electrode 2A and then an enzyme-free moisture-absorbing gel layer 9 is formed on the whole electrode portion of the substrate 1.

A method of measuring the concentration of ethanol gas by utilizing the ethanol biosensor manufactured according to the embodiments of the present invention will now be explained.

Figure 3:
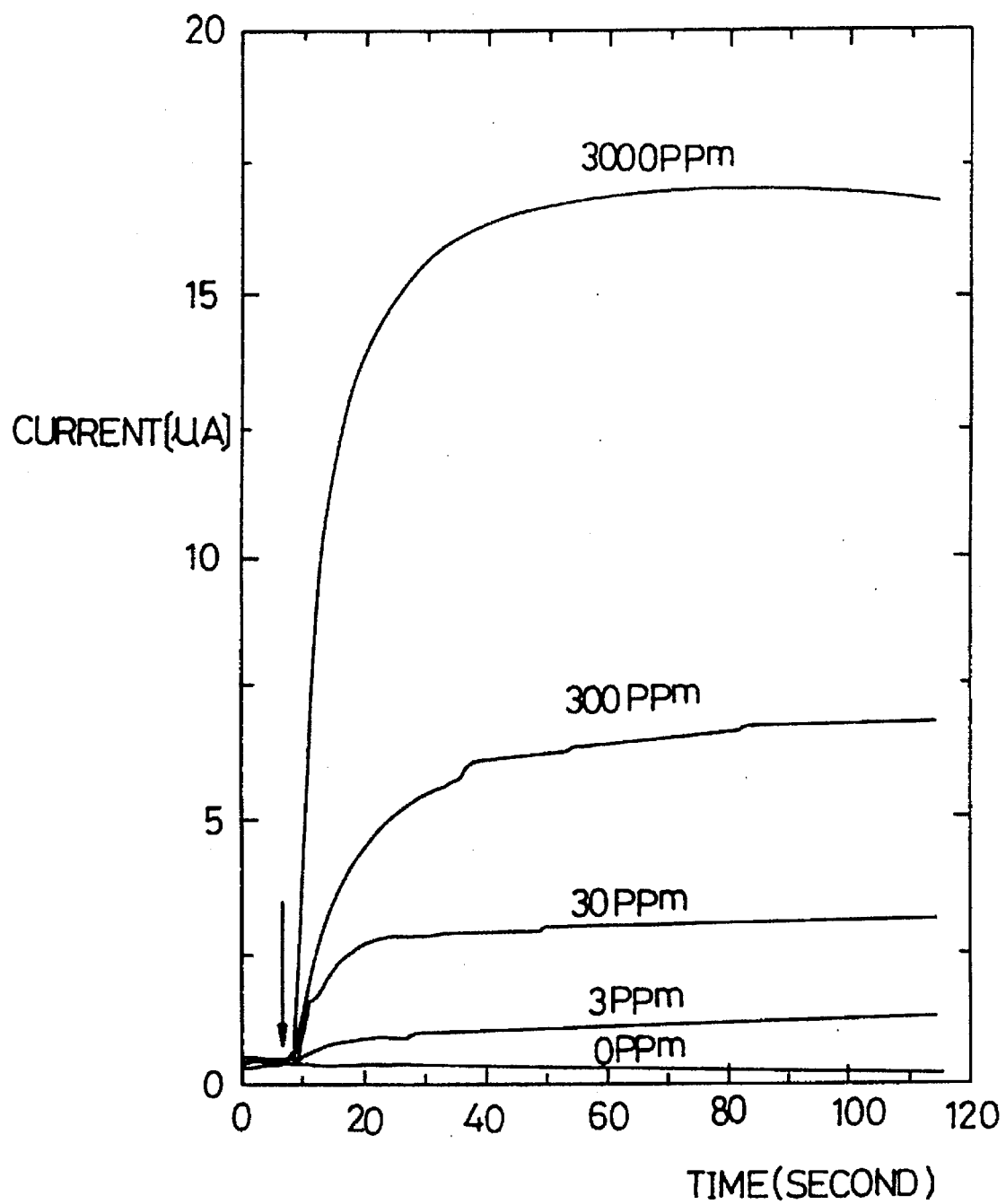
FIG. 3 is a graph explaining the response characteristics of the gas biosensor according to the present invention.

In order to operate the above-mentioned ethanol biosensor, an ordinary potentiostat may be used. While the electric potential difference between the working electrode and the reference electrode (Ag/AgCl) is determined to be about 650 mV, the chronoamperometric response to the ethanol gas gasified at about 25° C. is shown at FIG. 3. Specifically, the gas-phase ethanol gas is absorbed in the moisture-absorbing gel layer when the electric potential difference is about 650 mV, and thus the electrode-active material, i.e., NADH, is formed by enzymatic reaction of the enzyme immobilized on the moisture-absorbing gel layer. The formed NADH is oxidized to $NAD^+$ on the working electrode, causing a current to flow from the working electrode to the counter electrode, in proportion to the concentration of ethanol. If the moisture content of the enzyme-immobilized membrane is saturated, the biosensor shows a good response characteristic within the range of 0–3000 ppm of ethanol gas as shown in FIG. 3. The concentration of ethanol gas can be obtained by utilizing the steady-state current as shown in FIG. 3, or by measuring the initial reaction rate.

Meanwhile, if the two working electrodes 2A and 2B have the same area in another embodiment, a differential amplifying circuit may be employed in order to prevent the inhibiting effect of the sensor response due to other electrode-active materials except for enzymatic reaction. At this time, the enzyme-immobilized membrane 8 is formed only on the working electrode 2A, and the moisture-absorbing gel layer 9 is formed on the membrane. According to the ethanol biosensor having the above-mentioned structure, the influence of other electrode-active materials contained in gases generated in the human breathing can be prevented, and thus it can be used as a private alcohol checker along with a portable potentiostat apparatus.

Further, in case that the substrate is made of high molecular polymer materials such as PVC, polyethylene terephthalate, polyethylene, etc., and the electrodes are formed by printing carbon paste, in the manufacturing process of the thick film electrochemical device, each thick film electrochemical device can be manufactured at a low price.

From the foregoing, it will be apparent that the biosensor according to the present invention can rapidly and accurately measure and analyse a gas-phase specimen having even a low concentration, with the advantages such as small size, economic mass production, easiness to be used as a biosensor for one-time measurement, etc.. Specifically, the biosensor according to the present invention can be used as an alcohol checker for one-time measurement of ethanol gas generated in human breathing. Further, the biosensor according to the present invention can also be used for all enzymatic reaction systems including a system involved with co-enzyme, i.e., NAD NADH, such as formate dehydrogenase, carbon monoxide dehydrogenase, etc., and an oxidase reaction system which forms $H_2O_2$, such as alcohol oxidase.

While the present invention has been described and illustrated herein with reference to the preferred embodiments thereof, it will be understood by those skilled in the art that various changes in form and details may be made therein without departing from the spirit and scope of the invention.

What is claimed is:

1. A biosensor for measuring gas, comprising:
    a thick film electrochemical device having an insulating substrate, a plurality of electrodes formed on said substrate, a plurality of pads electrically connected to said electrodes, respectively, and an insulating layer; and
    a continuous moisture-absorbing electrolyte gel layer formed on said electrodes and, on at least one of said electrodes, said gel electrolyte layer has an enzyme immobilized layer.

2. A biosensor as claimed in claim 1, wherein said plurality of electrodes comprises a working electrode, a counter electrode and a reference electrode.

3. A biosensor as claimed in claim 1, wherein said plurality of electrodes comprises first and second working electrodes and a reference electrode.

4. A biosensor as claimed in claim 3, wherein an enzyme layer is formed only on said first working electrode, and an enzyme-free moisture-absorbing electrolyte gel layer is formed on said enzyme layer, said second working electrode and said reference electrode.

5. A biosensor as claimed in claim 1, wherein said immobilized enzyme consists of an enzyme group of oxidoreductase or hydrolase.

6. A biosensor as claimed in claim 5, wherein said enzyme group is one of alcohol dehydrogenase, carbon monoxide dehydrogenase, formate dehydrogenase and alcohol oxidase.

7. A biosensor as claimed in claim 1, wherein said moisture-absorbing gel layer is made of one of gelatin, polyacrylamide, alginate and agarose.

8. A biosensor as claimed in claim 7, wherein said moisture-absorbing gel layer includes potassium chloride.

9. A method of manufacturing a gas biosensor, comprising the steps of:
    preparing a thick film electrochemical device by forming on an insulating substrate a plurality of electrodes, a plurality of pads for electric connection with the electrodes, respectively, and an insulating layer; and
    forming a moisture-absorbing gel layer on the thick film electrochemical device by dropping on an electrode portion of the thick film electrochemical device an enzyme-mixed solution in which a moisture-absorbing gel solution and an enzyme solution are mixed together, and drying the dropped enzyme-mixed solution.

10. A method as claimed in claim 9, wherein the enzyme solution is prepared by dissolving an enzyme and a co-enzyme in a buffer solution.

11. A method as claimed in claim 9, wherein the moisture-absorbing gel solution is prepared by dissolving a moisture-absorbing gel such as gelatin in a potassium chloride solution.

\* \* \* \* \*